United States Patent
Krispel et al.

(10) Patent No.: US 6,512,813 B1
(45) Date of Patent: Jan. 28, 2003

(54) ROTATING STEREOTACTIC TREATMENT SYSTEM

(76) Inventors: Franz Krispel, 226 Warwick Dr., Walnut Creek, CA (US) 94598; Kahled Nawawi, 25 Grove Creek Ct., Lafayette, CA (US) 94549

( * ) Notice: Subject to any disclaimer, the term of this patent is extended or adjusted under 35 U.S.C. 154(b) by 0 days.

(21) Appl. No.: 09/980,675
(22) PCT Filed: May 2, 2000
(86) PCT No.: PCT/US00/11967
§ 371 (c)(1), (2), (4) Date: Oct. 30, 2001
(87) PCT Pub. No.: WO00/66223
PCT Pub. Date: Nov. 9, 2000

Related U.S. Application Data
(60) Provisional application No. 60/132,269, filed on May 3, 1999.

(51) Int. Cl.⁷ .................................................. A61N 5/10
(52) U.S. Cl. ............................................ 378/65; 378/64
(58) Field of Search ........................... 378/64, 65, 148, 378/149, 150, 151, 196

(56) References Cited

U.S. PATENT DOCUMENTS

| | | |
|---|---|---|
| 4,780,898 A | 10/1988 | Sundqvist |
| 5,448,611 A | 9/1995 | Kerjean |
| 5,528,653 A | 6/1996 | Song et al. |
| 5,537,452 A | 7/1996 | Shepherd et al. |
| 5,627,870 A | 5/1997 | Kopecky |
| 5,757,886 A | 5/1998 | Song |
| 6,044,126 A * | 3/2000 | Rousseau et al. ............ 378/65 |

* cited by examiner

Primary Examiner—Drew A. Dunn
Assistant Examiner—Allen C. Ho

(57) ABSTRACT

A system for isometric irradiation of target tissue from multiple radiation sources includes a structure supporting an oblique array of radiation sources disposed to rotate about an axis (28) coinciding with the longitudinal axis of a patient, such that individual sources describe non-overlapping trajectories on the surface of the patient. The sources are supported by asymmetric source carrier (24) within relatively limited angular region about said axis. The sources are collimated by selectable sets of apertures (31ai–31di) arranged on mutually independently rotatable rings (30a–30d), each such ring selectably capable of alignment with a sub-array (24a–24f) of sources to produce a variety of patterns and dynamic intensity modulations of the radiation flux.

14 Claims, 5 Drawing Sheets

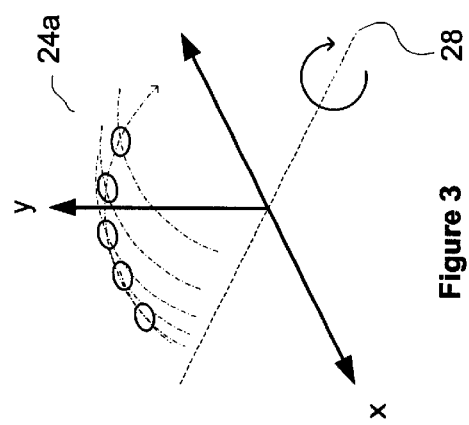
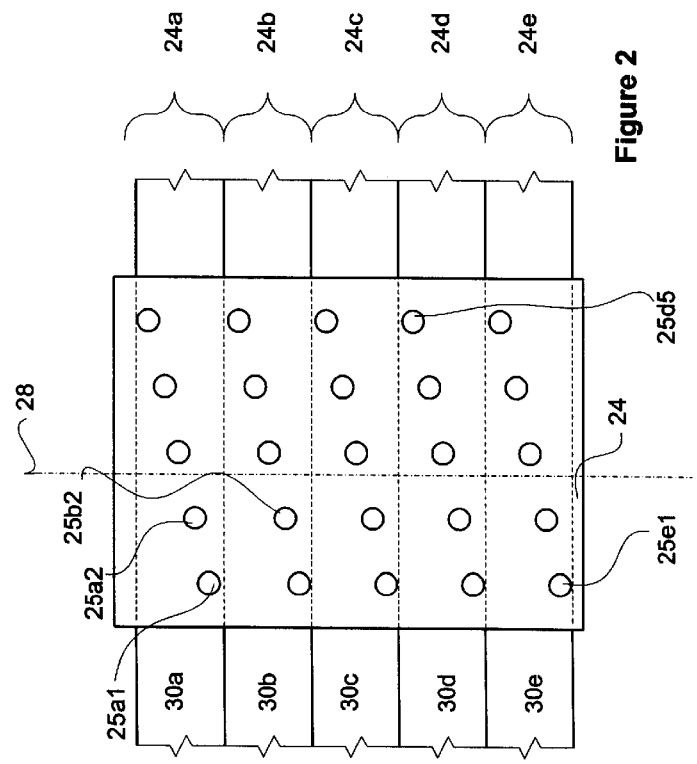
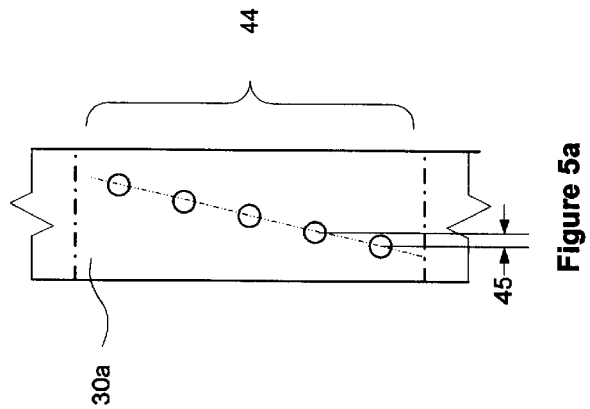
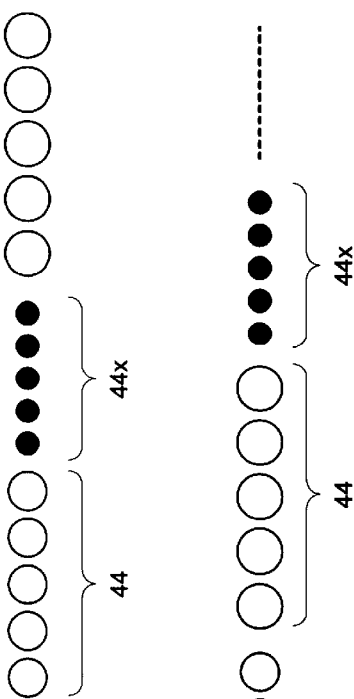

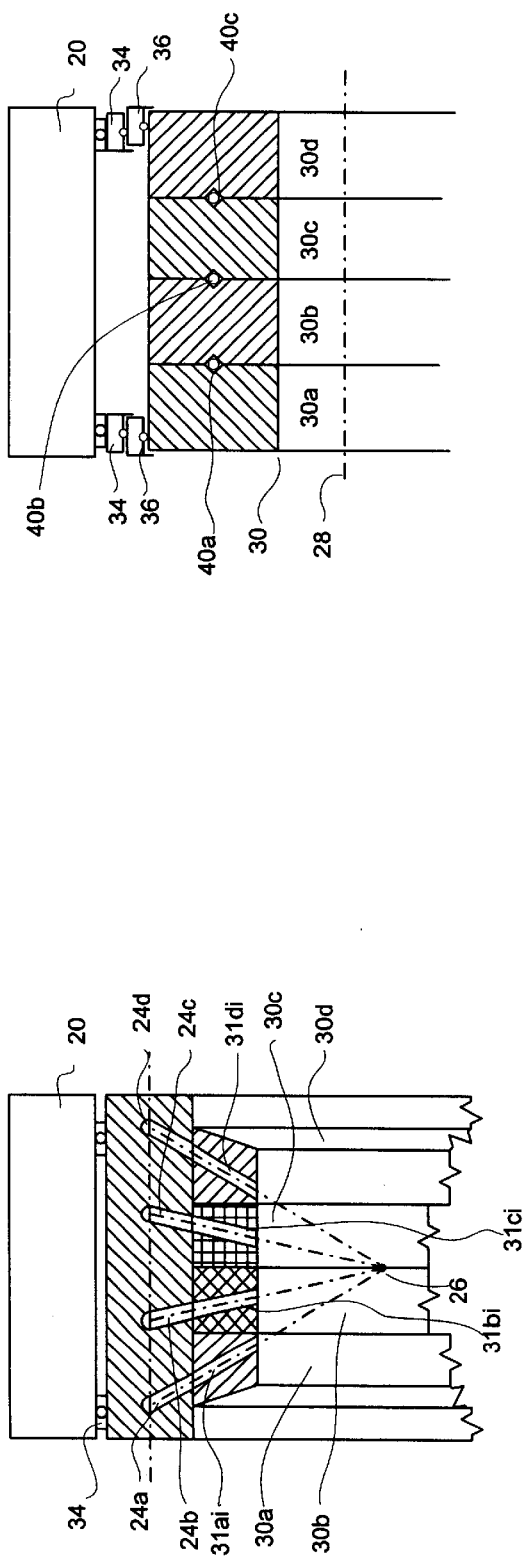
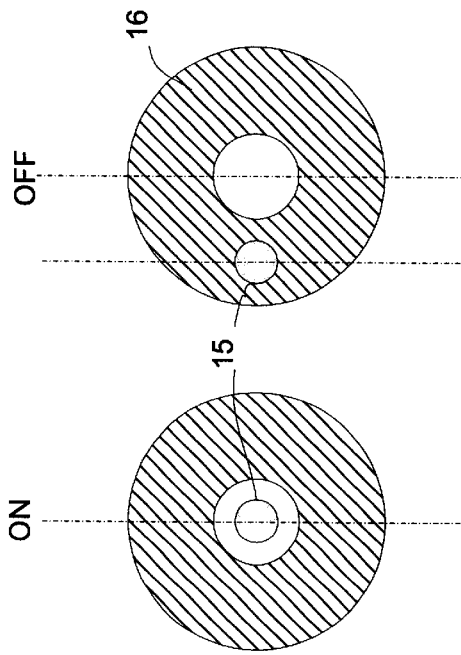
Figure 4b
Figure 5d
Figure 4a

US 6,512,813 B1

ROTATING STEREOTACTIC TREATMENT SYSTEM

This application claims the benefit of Provisional application Ser. No. 60/132,269, filed May 3, 1999.

FIELD OF THE INVENTION

The invention pertains to the field of stereotactic radio surgery and particularly relates to a system for this purpose using a rotating array of radiation sources.

BACKGROUND OF THE INVENTION

Therapeutic use of a flux of high energy photons dates from the early work of Roentgen. The object of the therapy is the destruction of a specifically defined volume of living tissue while sparing adjacent tissue. The development of method and apparatus for this purpose has generated a voluminous literature. In a more recent progression in this field, there has developed the use of plural radiation sources directed at the treatment voxel from diverse directions. Very high precision of radiation dose and dose distribution is achievable from this stereotactic approach. The treatment volumina typically range from 20 $cm^3$ to 0.5 $cm^3$ and precision direction of the radiation beam is required. Included among applications of this treatment are cancer metastasis, primary cancer of the brain, arterial-venous malformations, certain types of: facial pain, epilepsy, Alzheimer's disease, and Parkinson's disease.

One system of the prior art is the Leksell GamraKnife™. This system includes a semi-spherical source body containing a number of radiation sources enclosed by a thick radiation shield. The source body has open beam channels directed from the individual source locations radially inwards toward a common focal point. This is described in European Patent Publication EP-248774. In such a system, each of the multiple radiation sources provides only a small dose to intervening tissue, with the resulting maximum radiation dose available only at the common focal locus where the several radiation beams intersect. Accordingly, living tissue at the focal locus will be effectively killed without substantial harm to surrounding tissue after treatment for a prescribed time. Thus, this system of the prior art uses a great many radiation sources, as for example $201^{60}Co$ sources of equal activity, regularly arranged on a hemisphere. With the increasing number of sources of less activity, the relative radiation exposure of healthy tissue is substantially decreased relative to the tissue at the focal volume. Such a construction requires a corresponding increase of heavy shielding material resulting in considerable weight and volume. It is also necessary to achieve an orderly and accurate array of hundreds of bores in the structure, arranged on the surface of a hemisphere of large diameter and defining a common focal point with precision. The manufacture of this equipment is a difficult and expensive exercise. Moreover, this static arrangement of many radioactive sources leads to a very high cost in the procurement and handling of many sources which must exhibit a high uniformity in specific activity. Fewer radiation sources would be preferable in such a stereotactic system.

Another prior art system is disclosed in U.S. Pat. Nos. 5,528,653 and 5,757,886, each assigned to Song. In this system, 30 sources are uniformly distributed (azimuthally) around a half sphere which is adapted to rotate about its symmetry axis during patient treatment. The rotational axis coincides roughly with the longitudinal axis of the patient. This prior art system further includes a concentric collimator hemisphere disposed within the source body hemisphere. This collimator is adapted to be rotated independently of the source body hemisphere to align a desired size aperture with the corresponding source. The collimator is then locked to the source carrier hemisphere and the rotation of the source collimator assembly allows stereotacticaly irradiating the patient with selected size radiation beams.

A rotating symmetrical source system as described is disadvantaged compared to a static system as described in that individual sources or groups of sources can not be blocked independently from each other. Such selective blocking is desired or necessary, for example to avoid irradiation of specifically sensitive tissue adjacent the treated volume.

Both the static and rotating systems of prior art are further deficient or undesirable in their large size, weight and moment of inertia; inapplicability for body parts other than the head; claustrophobic effect of the treatment chamber; need for shielding doors to reduce radiation levels outside the treatment chamber; loss of focal precision due to one sided cantilever bearing of the rotating mechanism; and, absence of a preferred standby or service mode shielding position. Moreover, the prior art is not adaptable to dynamic modulation of the collimated flux during a treatment.

SUMMARY OF THE INVENTION

The present invention implements a novel design for a stereotactic radio surgery system wherein the irradiation facility, in one geometry, comprises an open structure requiring minimal shielding while facilitating radiation treatment locations other than the head. This is achieved by relationship of axial and radial dimensions for the patient acceptance region and the mutual arrangement of an asymmetric rotating source carrier of limited angular interval diametrically opposite a beam catcher and counterweight structure adapted to minimize scattered radiation. The source array has the form of an oblique two dimensional array of source locations which allows for a selected pattern of sources of selectable collimation and strengths. The collimation function is obtained with a collimator structure composed of annular collimator rings, adapted for independent relative rotation, each capable of alignment with an approximated one dimensional sub-array of the source array. A variety of aperture sizes are available by rotation of a collimator ring with respect to the corresponding source sub-array, after which the collimator ring(s) synchronize with the source subarray(s) for irradiation of the designated tissue volume.

The independent synchronous rotation of source array and collimator structure is maintained to a high degree of precision and a controlled relative rotation for a short period of time enabling alignment of a different collimator array with the source array during a specified portion of a revolution. Thus the controlled independence of the rotating source and collimator members affords dynamic modulation capability for treatment dose.

Apart from reduction of the weight of shielding, the open structure of this geometry permits superposing the focal locus on body regions of the patient other than the head.

Another geometry which consists of a half closed embodiment particularly suited to cranial treatment employs an asymmetric array of sources disposed within a limited sector of a spherical shell. A set of collimator arrays is selectable on an inner collimating structure rotating coaxially with the source array sector.

BRIEF DESCRIPTION OF THE DRAWINGS

FIG. 2 shows an array of mutually offset sources.

FIG. 3 is a schematic illustration of the rotational plane of irradiation.

FIG. 4a partially shows an embodiment featuring multiple independent partial collimators.

FIG. 4b illustrates the mutual relationship of the partial collimators.

FIG. 5a shows a collimator aperture set mapped onto a plane.

FIG. 5b shows one sequential arrangement of null and non-null apertures

FIG. 5c shows another sequential arrangement of aperture sets.

FIG. 5d represents an arrangement for fast transition to an alternate null radiating position.

FIG. 7b represents a collimator array for the source carrier of FIG. 7a.

While the invention is susceptible to various modifications and alternative forms, the above figures are presented by way of example and/or for assistance to understanding the structure or phenomena. It should be understood, however, that the description herein of the specific embodiments is not intended to limit the invention to the particular forms disclosed, but rather, the intention is to cover all modifications, equivalents, and alternatives falling within the spirit and scope of the invention as defined in the appended claims.

DETAILED DESCRIPTION OF THE INVENTIVE SYSTEM

Figure 1A:
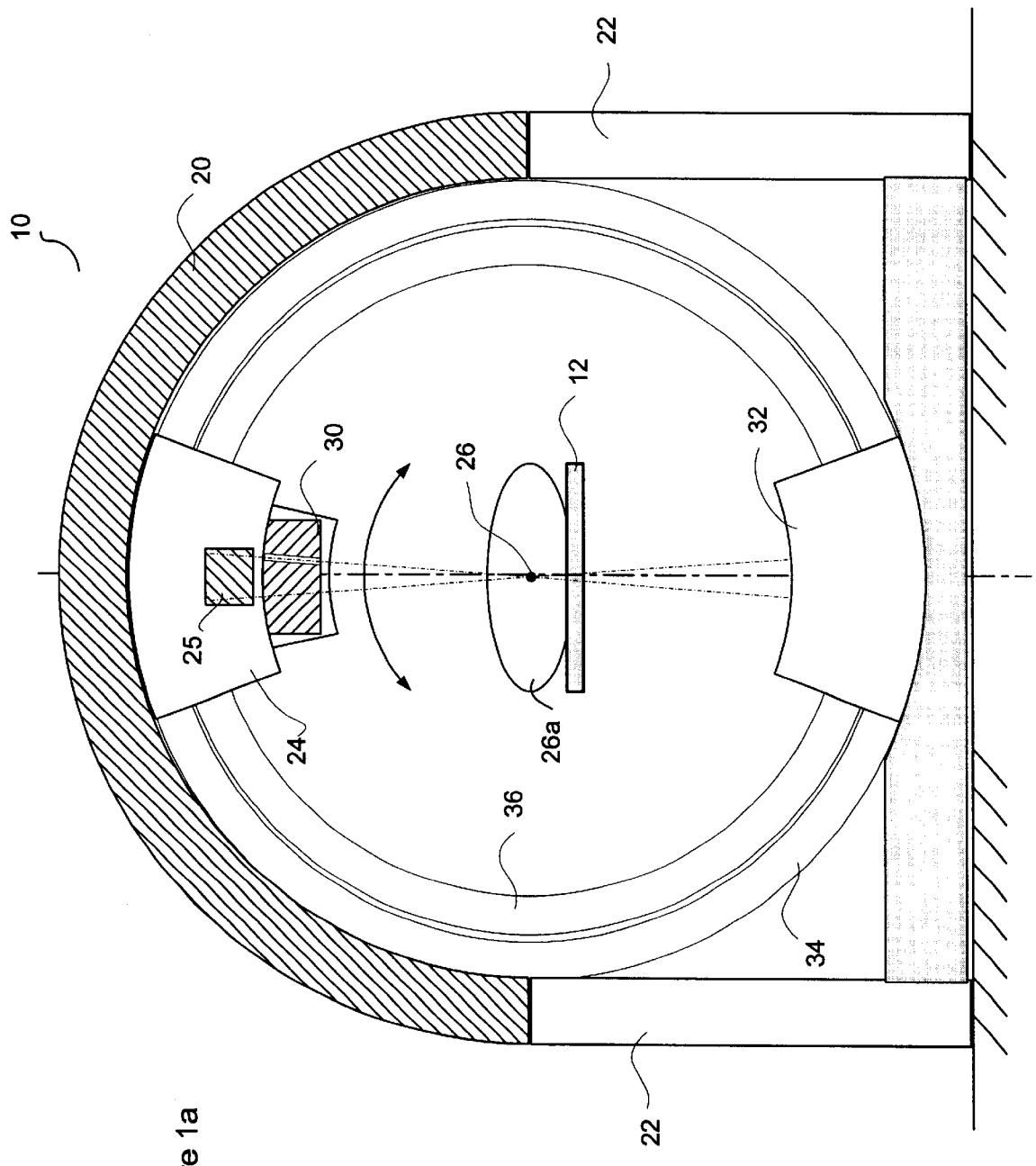
FIG. 1a is a schematic view along the patient axis of the inventive system.
Figure 1B:
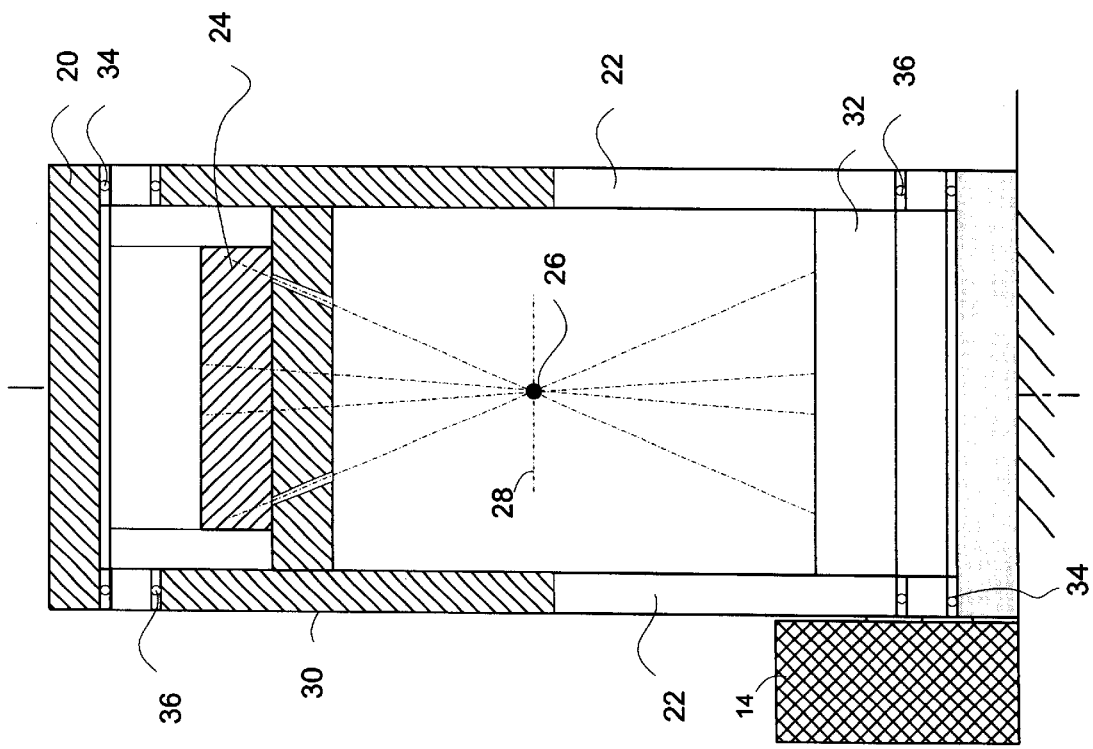
FIG. 1b is a schematic view perpendicular to the patient axis of the inventive system.

Turning now to FIG. 1a there is shown a system 10 comprising a radiation shield 20 with supporting structures 22. At least one source array carrier 24 is supported for rotation about axis 28. A patient treatment table 12 is provided to support a patient treated by irradiation from the asymmetrical source array carrier 24 in combination with collimator 30. The source array is characterized by a number of bores in a carrier body which are directed toward a common intersection. A bore is intended to house a radiation source in use and to define a radiation channel for its gross direction of the radiation flux from that source. $Co^{60}$ is a typical choice for the radiation source. The asymmetrical source array 24 subtends an angular interval, or sector, in the range of 20° to 60° in the plane of rotation. A beam catcher/counterweight 32 is disposed diametrically opposite the source carrier 24. FIG. 1b provides additional perspective from the side view. Bearings set 34 support the source carrier 24 and beam catcher/counterweight 32 in relation to the system 10. Another bearing set 36 supports collimator 30 relative to source array carrier 24. The outer race of bearing 36 can alternatively be mounted directly to structure 20. The source array carrier 24 and collimator 30 define intersecting source axes providing for radiation beams intersecting at a predesignated focal locus 26 inside patient 26a shown as a saggital cross section on the rotation axis 28. The source array subtends an axial angular increment of about 30°. The motor and drive and motion controllers for same are schematically shown as block 14. Rotation rates of the order of a few rpm are typical.

FIG. 2 shows a mapping of the source array 24 onto a plane as viewed perpendicular to the axis 28 with respect to collimator sets 30a, 30b, . . . etc. The source array 24 preferably has the form of an oblique array of sources in corresponding bores 25a1, 25a2 . . . 25b1, 25b2 . . . etc. Sources are exclusively disposed in a limited angular sector of source carrier 24 for rotation about axis 28. The axes of the bores 25xi are directed radially inward to intersect at a common locus 26. Adjacent sources are offset as indicated, in order that projected trajectories of the sources will not coincide on tissue intervening between sources and the focal locus 26. The collimator 30 preferably has the structure as shown in FIG. 4a wherein the collimator 30 is an assembly of partial collimator rings 30a, 30b, 30c, 30d, etc. Each of these partial collimators corresponds to a source sub-array 24a, 24b, 24c, 24d. Moreover, each partial collimator is characterized by a plurality of sets of apertures 31i, 31j, etc wherein alignment of a set of apertures 31ai with corresponding sub-array 24a produces a set of defined radiation beams which intersect at the predesignated focal locus 26. For a source of given activity and energy, to the design of suitable collimation, including the materials, geometry and the like, are well within the knowledge of one of skill in the art.

FIG. 4b shows the manner wherein the partial collimators 30a, 30b, etc. are supported through a set of self-carrying bearings 40a, 40b, etc. The entire collimator assembly 30 is supported with respect to the supporting structures 20 through main collimator bearings 36.

In operation, a synchronizing arrangement, not shown, represents one embodiment for securing the partial collimators 30a, 30b, etc and the source subarrays 24a, 24b, etc. together for rotation as a single collimator ring 30 and source array 24, after the desired collimator apertures are aligned with respective source sub-arrays. In this arrangement, the collimator rings are independently driven through motors and drive trains (not shown) and synchronized to each other and to the source carrier in a known manner via electronic position and rotation sensors within an electronic closed loop feedback system provided by a conventional motion controller, such as the 5 axis controller manufactured by Galil Motion Control, Inc of Mountain View, Calif. Synchronization apparatus of this type, for this purpose is well known to one of skill in the art and need not be described in detail for present purposes. In one embodiment, as an example, the collimator rings are each driven by an electrical motor through chain and sprocket to avoid backlash. The rotational position and speed is conventionally derived from an angular encoder driven off the chain in a chain driven arrangement). Alternatively, an optical encoding device may be employed for this function.

In FIG. 3, the rotation of a single sub-array 24a about the rotation axis 28 is shown. Each aperture of subarray 24x rotates in a plane offset from the adjacent aperture along axis 28. Other sub-arrays, offset as described are distributed axially, that is, along the direction of axis 28.

FIG. 5a shows an arrangement of one set 44 of collimator apertures for a portion of single collimator ring 30a, for example, as mapped onto a plane and viewed from the rotation axis 28. Each aperture set 44 comprises a plurality of individual apertures which may be aligned with a corresponding source sub-array 24a, for example. Thus each aperture of a set 44 is offset from the adjacent aperture in the manner 45 of the offset character of the source sub-array elements. The offset 45 is selected such that during radiation, each individual source—collimator combination radiates tissue through a unique slice, preferably without overlap. An aperture set 44x is conveniently included for null flux. The ability to rapidly change between different aperture sets is facilitated by the sequence symbolically shown in figure 5b wherein a null set of apertures is situated between each non-null aperture set. Each set of apertures in this arrangement follows (is followed by) a null set 44x of (plugged) apertures. This provides one arrangement for achieving a null flux interval during which relative angular displacement of the source carrier and collimator ring is adjusted through the agency of the synchronization module. FIG. 5c symbolically represents another sequence of aperture sets. It will be apparent that the spacing of aperture sets is limited only by the spacing of the corresponding source arrays. FIG. 5d shows another way of achieving a null flux condition. A source 15 is aligned with the shielding body portion 16 of the collimator to absorb the radiation flux in the same manner as the null aperture set 44x of FIG. 5b is interposed in the radiation flux for this purpose. In this arrangement the dimensions of the shielding body portion 16 of the collimator has sufficient thickness and aperture spacing to intercept and absorb the beams, thus reducing the radiation leakage level to medically acceptable levels.

The ability to dynamically alter the radiation flux in the course of each rotation allows the sparing of particularly vulnerable tissue from radiation. One example is the interposition of blank apertures during a cranial treatment during that angular portion of the source carrier orbit where the eyes would otherwise be within the radiation trajectory.

The switching between collimator sizes or shutting off the radiation during the course of an ongoing treatment is achieved by a small relative position change between the source array and the collimator array. For fast switching in the order of fractions of a second, the relative angular position between these two synchronously rotating systems has to change sufficiently in a short period of time. In a preferred embodiment, this is accomplished by braking one rotating structure while accelerating the other structure at the same time.

Figure 6:
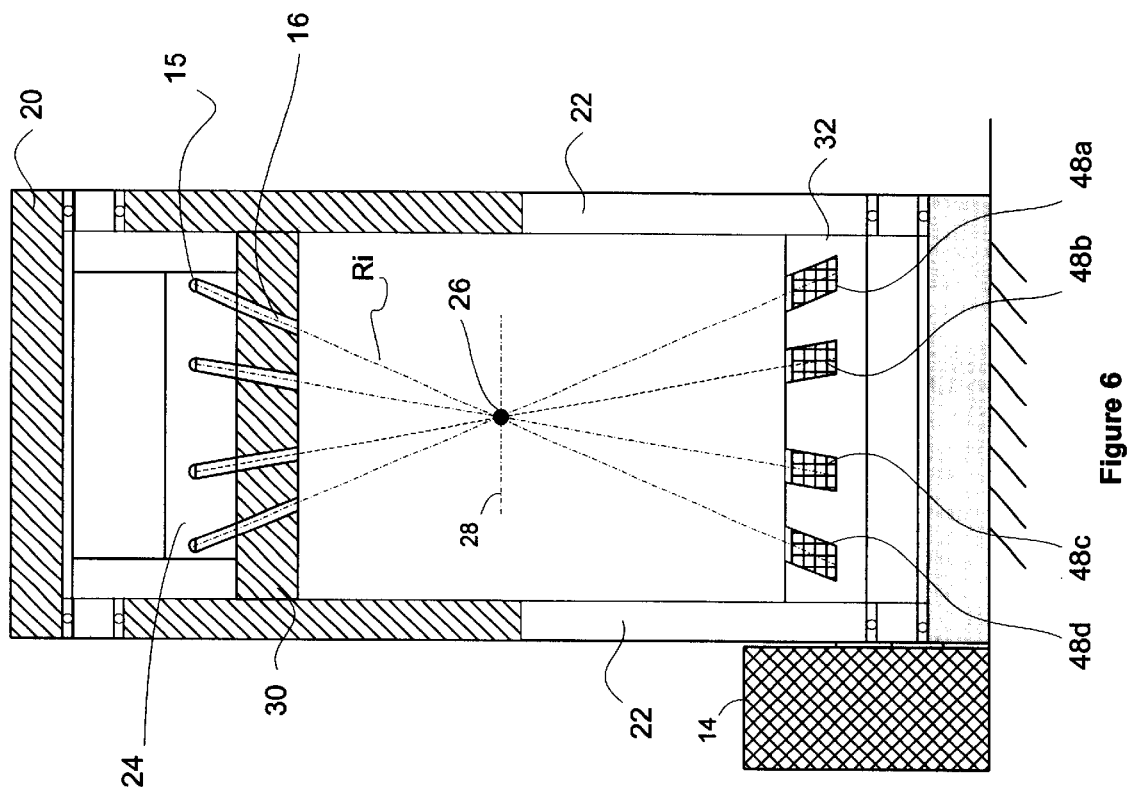
FIG. 6 is a section of the system of FIG. 1a and 1b particularly illustrating the beam catcher arrangement.

FIG. 6 elaborates the geometrical differences between sources which are dispersed along the axis, as projected thereon. Although the individual source axes are desired to intersect at the focal locus 26, the sources need not be arranged on a spherical shell, but may be disposed along a surface which is parallel to, or coaxial with the axis of rotation 28. In such instance, the distance Ri of each source to the focal locus 26 is determined geometrically. The flux densities of the several sources vary inversely with the square of the respective distance resulting in divergence of the collimated flux. In the present invention, the relative strength of selected source elements of the source array 24 are selected to compensate for this geometric variation. Selection of aperture size to compensate this variation may not be appropriate in many situations where the cross sectional size of individual radiation beams is subject to specific treatment planning parameters. The open structure of the present invention is facilitated first by arrangement of the source elements of source array 24 to permit no rectilinear propagation from a source to a location outside the structure 10. Next, it is desirable to baffle scattering of photon beams in a beam catching structure 32. As shown in FIG. 6, scattered photons are preferably degraded by multiple scattering within counterbores 48a, 48b, etc. The beam baffling structure preferably serves as a counterweight to source array 24 (including collimators). If desired, the beam baffling function may also be incorporated within source carrier 24 and the beam baffle-counterweight 32 is then designed to also serve as a second source array.

The beam sink counterweight structure 32, together with the source carrier and collimation structure 30, in another variation of this embodiment, are deliberately arranged to exhibit an asymmetric distribution in weight about the rotational axis to provide a fail-safe operating mode. Upon loss of power during treatment, for example, the asymmetry causes the apparatus to come to rest at an equilibrium position where the radiation beams are blocked by shielding such as collimator null apertures 44x. The asymmetric weight distribution of the source carrier and collimator structure forces both structures to assume the equilibrium position characterized by the closure of radiation bores $25_{xy}$. Rotational motions of the source carrier and the collimator rings are differentially damped by the respective drive mechanisms causing relative angular displacement of the source carrier and collimator rings. A spring loaded plunger actuated by loss of solenoid power engages the collimator ring with the source carrier to align null aperture sets with respective source bores effectively terminating the radiation treatment. At the equilibrium (rest) position the source array is directed in a desired orientation with respect to structure 20 that affords ambient protection from leakage radiation as a consequence of the narrow azimuthal confinement of the radiation sources.

Figure 7B:
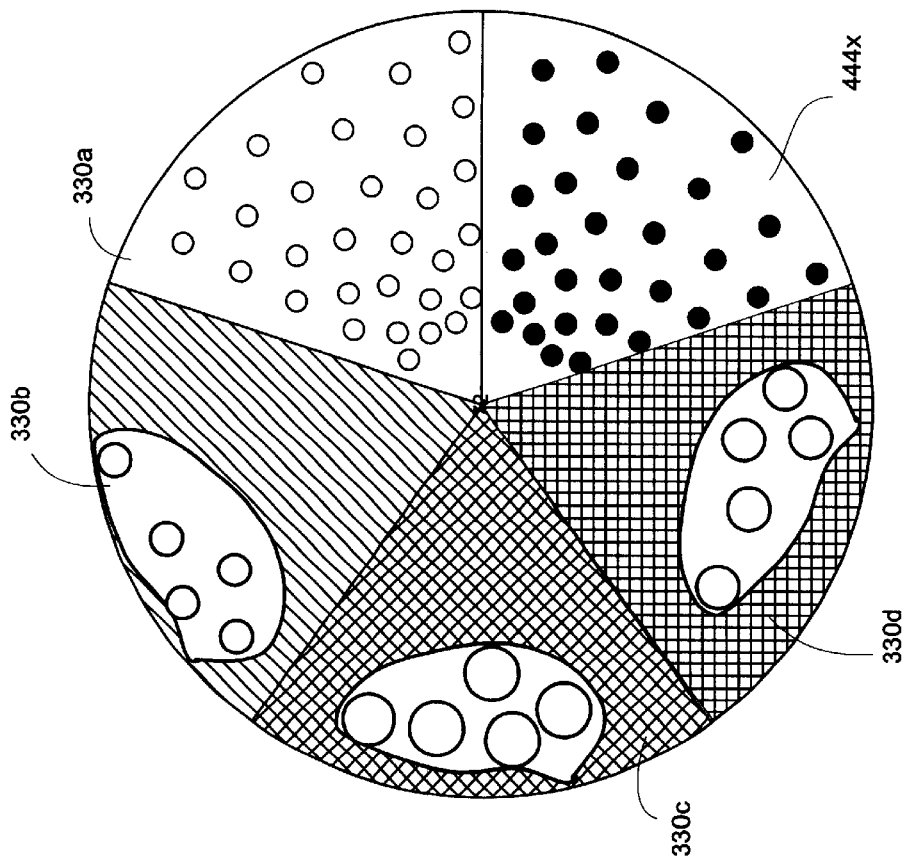
Figure 7A:
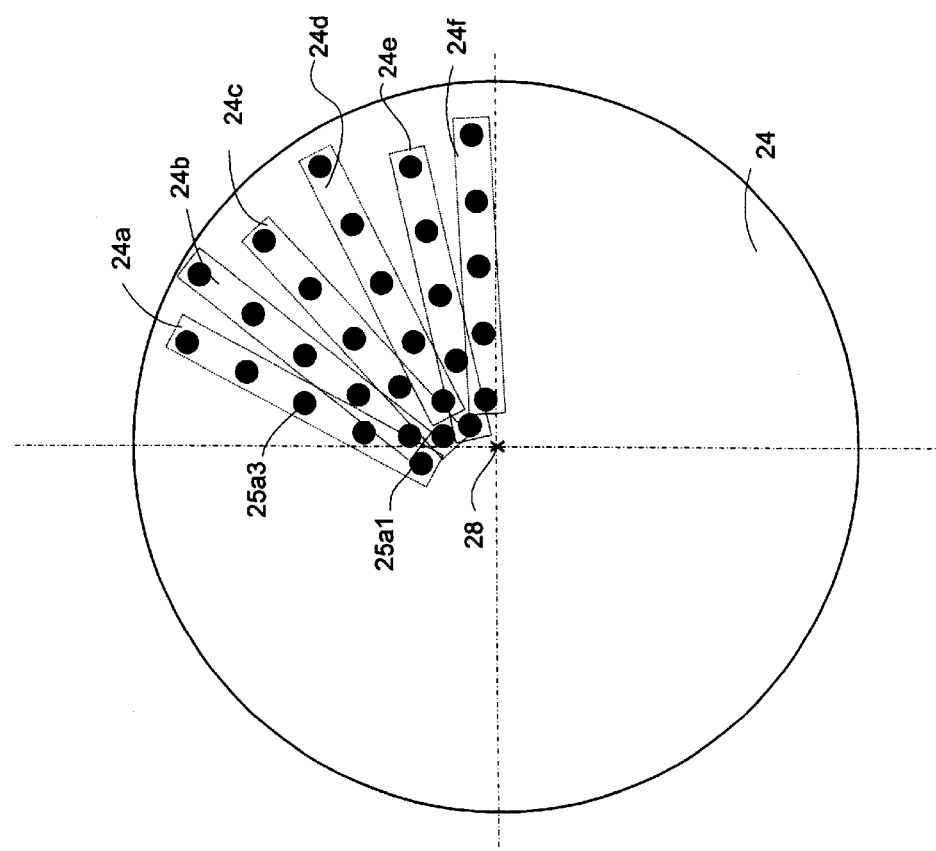
FIG. 7a represents a preferred arrangement of sources within a limited sector for a system of single ended geometry.

The invention is easily adapted to an embodiment especially useful for cranial treatment. In this single ended geometry, the source array is disposed in a limited angular region of a hemispherical shell, or portion thereof, for rotation about the symmetry axis of the hemisphere. The collimator arrays are supported in similar corresponding angular regions of an inner hemispherical shell supported to permit rotation independent of the rotation of the source carrier. FIG. 7a shows an arrangement (mapped to a plane) of sources 25a, distributed on a limited angular sector, for example, 30 sources distributed within a 72° sector. FIG. 7b represents a suitable collimator consisting of five 72° sectors, four of which contain an aperture array matching the source array of FIG. 7a. One sector, 444x, is plugged (with tungsten or depleted uranium solid inserts) to assure a null radiation condition. The remaining sectors 330a, 330b, 330c and 330d contain collimating apertures of selected size and properties as depicted in cutaway fashion in FIG. 7b. Relative rotation of the collimator and source carrier is established from the independent drive mechanisms and the stabilization to angular synchrony is established in known fashion with electronic rotation and position sensors in a feedback system as is commonly known. The asymmetry of the source geometry facilitates an equilibrium position and permits a less massive structure. The degree of asymmetry introduces an unbalanced torque of proportional magnitude which has been observed to be within the limits of the synchrony control system, motor torque and gear ratio to maintain relative angular position during rotation to 1 part in $10^4$.

The overall system is driven by a set of motors controlled by a multi-axis motion controller that is capable of high accuracy for each axis. The drive system described is depicted in FIG. 1b as item 14.

While there have been shown and described what are at present considered the preferred embodiments of the present invention, it will be obvious to those skilled in the art that various changes and modifications may be made therein without departing from the scope of the invention as defined by the appended claims.

What is claimed is:

1. An apparatus for general radiotherapeutic application including radiosurgery, comprising (a) a source carrier for supporting an array of radiation sources, said source carrier adapted for rotation about a first axis, (b) a collimating structure for directing radiation flux emanating from each said radiation source radially inward along a respective collimator axis through a radiation flux limiting aperture toward a substantially common locus on said first axis, said collimating structure adapted for angular displacement in relation to said source carrier about said first axis characterized in that said radiation sources are distributed within a narrow azimuthal region of about 20° to 72° about said first axis and a sub-array of radiation flux limiting apertures is provided for each said radiation source and the several sub-arrays are adapted to selectably align one such flux limiting aperture with each said radiation source, whereby a plurality of different solid angles for each said radiation source may be selected.

2. The apparatus of claim 1 wherein said source carrier comprises a limited angular sector sufficient to include said narrow azimuthal region.

3. The apparatus of claim 1 or 2 wherein said source carrier and collimator structure is distributed over a limited solid angle in a plane containing said first axis.

4. The apparatus of claim 3 further comprising a beam sink carrier disposed symmetrically with said source carrier and collimating structure about said first axis, said beam sink carrier comprising a plurality of channels, each said channel having a channel axis radially directed toward said focus and colinear with a corresponding collimator axis.

5. The apparatus of claim 4 wherein said beam sink structure comprises said additional source carrier and said beam channels comprise another collimator structure whereby the radiation flux incident on said focus is increased.

6. The apparatus of claim 4 wherein said beam sink carrier exhibits a selected mass asymmetry in respect of said source carrier whereby said source carrier assumes an equilibrium position of desired orientation.

7. The apparatus of claim 3 wherein said apparatus has at least one relatively open area at a first axial extreme and said source carrier and collimator structure has such extension along said first axis in relation to said limited solid angle whereby radiation from said apertures of said collimator structure does not escape any said open area.

8. The apparatus of claim 1 comprising a shielding member spaced from said source carrier and collimator structure and having an extension along the direction of said first axis and a width perpendicular to such axis sufficient to intercept radiation in an outward radial direction from each said radiation sources.

9. The apparatus of claim 1 comprising at least one additional source carrier and collimator structures, said additional source carrier and collimator structure providing another plurality of radiation sources directed toward another substantially common locus on said first axis.

10. The apparatus of claim 1 wherein said array of radiation sources comprises a plurality of source sub-arrays and said collimator structure comprises a like plurality of collimation substructures, each said collimation substructure supporting a said sub-array of radiation flux limiting apertures, each said aperture of said sub-array of apertures having selected dimensions.

11. In apparatus for general radiotherapeutic application to tissue, including radiosurgery, said apparatus comprising a structure forming a shielding body and support for first and second rotating structures, said first rotating structure comprising a source carrier for housing a plurality of radiation sources in corresponding bores and said second structure comprising a collimating structure for defining a radially inwardly directed radiation beam from each respective said source through said bore toward a common locus on the axis of said rotation, said collimating structure comprising a plurality of spaced flux limiting apertures disposed for selective alignment with each said radiation sources for defining a corresponding said inwardly directed radiation beams, the method of sparing tissue, comprising (a) irradiating said tissue from each said source through first selected flux limiting apertures while rotating both said rotating structures at a common angular velocity, (b) establishing the angular proximity of said inwardly directed radiation beam to tissue designated for sparing during said rotation, (c) causing rapid relative rotation of said collimating structure relative to said source carrier by an angle sufficient to seal said bore by a spaced portion of said collimating structure whereby said radiotherapeutic application is interrupted.

12. The method of claim 11 further comprising, (a) detecting the angular position corresponding to a boundary indicating the location of tissue for radiation treatment, (b) reversing said relative rotation of step (b) to re-establish the alignment of said radiation sources with said corresponding apertures, whereby said radiotherapeutic application is resumed at said common angular velocity.

13. The method of claim 12 wherein step (c) comprises causing further said relative rotation for aligning selected flux limiting apertures with said corresponding radiation sources during a portion of said rotation.

14. The method of claim 11 wherein said step of causing rapid relative rotation comprises decelerating rotation of one said rotating structure and accelerating the rotation of the other rotating structure.

* * * * *